United States Patent [19]
Kim et al.

[11] Patent Number: 5,241,959
[45] Date of Patent: * Sep. 7, 1993

[54] THERAPEUTIC, PORTABLE WATER BED ASSEMBLY HAVING A WATER HEATING SYSTEM

[76] Inventors: Yong Hak Kim; Soon Ja Kim, both of 330 S. Parrish St., Baltimore, Md. 21223

[*] Notice: The portion of the term of this patent subsequent to Sep. 15, 2009 has been disclaimed.

[21] Appl. No.: 904,576

[22] Filed: Jun. 26, 1992

[51] Int. Cl.5 ............... A47C 21/00; A63F 7/00
[52] U.S. Cl. ........................... 607/104; 5/421; 607/96
[58] Field of Search ............ 128/376, 377, 399–403; 5/284, 8, 422, 421

[56] References Cited

U.S. PATENT DOCUMENTS

| | | | |
|---|---|---|---|
| 333,820 | 1/1886 | Bowman | 5/284 |
| 385,865 | 7/1888 | Lewis | 5/422 |
| 1,212,479 | 1/1917 | Hall | 5/422 |
| 3,008,176 | 11/1961 | Paine | 5/8 |
| 4,218,791 | 8/1980 | Itoku | 5/284 |
| 4,648,141 | 3/1987 | Mansouris | 5/8 |
| 4,974,272 | 12/1990 | Liu | 5/422 |
| 5,146,633 | 9/1992 | Kim | 5/284 |

Primary Examiner—Mark S. Graham
Attorney, Agent, or Firm—Birch, Stewart, Kolasch & Birch

[57] ABSTRACT

A therapeutic, portable bed assembly having a pair of beds, includes an electric water heating system disposed within a base member of the bed, an U-shaped tube disposed on a circumferential edge of the bed which functions as a water tank, a serpentine configured water pipe extending through a concrete plate of the base member, and a pad member containing mugwort herb, disposed on a laminated paper cover on the concrete plate, whereby the bed can be easily moved and a vapor from the cotton pad can warm and treat the human body lying on the bed.

8 Claims, 2 Drawing Sheets

THERAPEUTIC, PORTABLE WATER BED ASSEMBLY HAVING A WATER HEATING SYSTEM

BACKGROUND OF THE INVENTION

1. Field of the Invention

The present invention relates to a therapeutic, portable bed assembly provided with a heating system and more particularly, to a portable water heating bed including a base member, a serpentine configured water pipe extending through the base member, and a water heater, whereby the portable water heating bed assembly can warm a person lying on a pad on the bed by circulating hot water in the water pipe through the water heater attached to the base member.

2. Description of the Prior Art

Various types of water heating beds are well known in the art. Such prior art water heating beds include a separate water heating system and a fixed base bed communicating with to the water heating system through a water pipe as shown in U.S. Pat. Nos. 17,102 to Lefebure, 825,763 to Schaefer, 1,121,277 to Mitchell, and 1,817,277 to Uhlig.

Also, various types of water heating pads are well known in the art. Such prior art water heating pads include a water pipe disposed therein and a separate or composite electric heater for heating the water disposed in the pad as shown in U.S. Pat. Nos. 4,114,620 to Moore et al, 4,149,541 to Gammons et al, 4,561,441 to Kolodziej, and 4,884,304 to Elkins.

However, such prior art devices suffer from a number of problems such as, for example, (a) it is very difficult to move the bed with the heating system, (b) it is complicated in structure such as a separate water tank, a separate heater, etc., (c) it is not expected to achieve a treatment effect for the human body, and (d) it is inconvenient to move due to a separate water heater from the bed compared with a bed having a water heater of the present invention.

In order to avoid the above described problems, the present inventors have filed U.S. patent application Ser. No. 07/788,229, filed Nov. 4, 1991 and now U.S. Pat. No. 5,146,633 which relates to a therapeutic, portable bed including an electric water heating system attached to and disposed within a base member of the bed, a hollow headboard of the bed, which functions as a water tank, a serpentine configured water pipe extending through a concrete plate of the base member, and a cotton pad member containing mugwort herb, disposed on a laminated paper cover on the concrete plate, whereby the bed can be easily moved and a vapor from the cotton pad can warm and treat the human body lying on the bed.

The present inventors have also filed U.S. patent application Ser. No. 07/864,854, filed Apr. 7, 1992, relates a therapeutic, portable folding chair provided with a heating system, which includes a base member, a serpentine configured water pipe, a hollow top portion of the back which functions as a water tank, a water heater attached to and disposed within the base member, and a mugwort herb pad disposed on the base member, whereby the folding chair can be easily moved and a vapor generated from the pad heated by the water pipe through the water heater warms and treats the human body sitting thereon or lying on a bed converted from the folding chair. However, these therapeutic, portable beds have some disadvantages such as, for example, it is complicated to have a water tank in a headboard and a chair back, and it is difficult to transport since these beds are heavy.

SUMMARY OF THE INVENTION

Accordingly, it is an object of the present invention to provide an improved therapeutic, portable water heating bed for warming a person lying on the bed, which eliminates the above problems encountered with conventional heating beds.

Another object of the present invention is to provide a portable water heating bed assembly including a pair of beds for assembling with and disassembling from each other, which includes each bed having a base member, a serpentine configured water pipe extending through the base member, a water tube disposed on a circumferential edge of the base member, a water heater attached to and disposed within the base member, and a pad containing mugwort herb, whereby when a plug of the water heater is connected to a power source, the hot water is easily circulated within the water pipe and a vapor generated from the pad penetrates and treats a desired region of the human body lying on the bed.

A further object of the present invention is to provide a portable water heating bed which is simple in construction, compact for portability, inexpensive to manufacture, durable in use, and refined in appearance.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a therapeutic, portable bed assembly having a pair of beds, includes an electric water heating system attached to and disposed within a base member of the bed, a U-shaped tube disposed on a circumferential edge of the bed which functions as a water tank, a serpentine configured water pipe extending through a concrete plate of the base member, and a pad member containing mugwort herb, disposed on a laminated paper cover on the concrete plate, whereby the bed can be easily moved and a vapor from the cotton pad can warm and treat the human body lying on the bed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Figure 1:
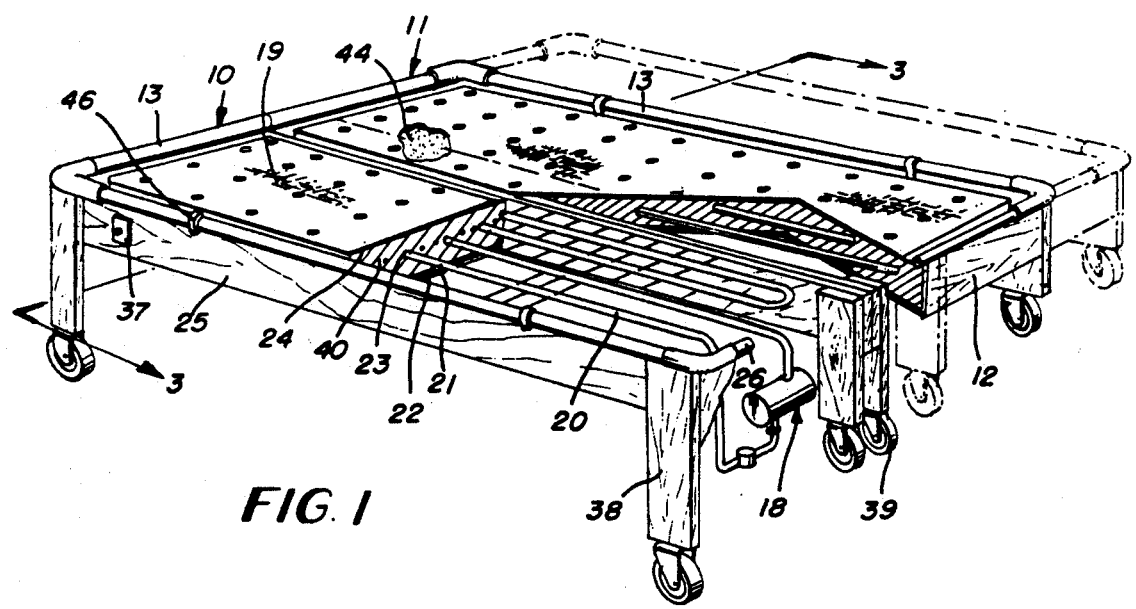
FIG. 1 is a perspective view of the therapeutic, portable water heating bed containing cut-away portions in order to illustrate the construction of the water heating bed assembly according to the present invention.
Figure 2:
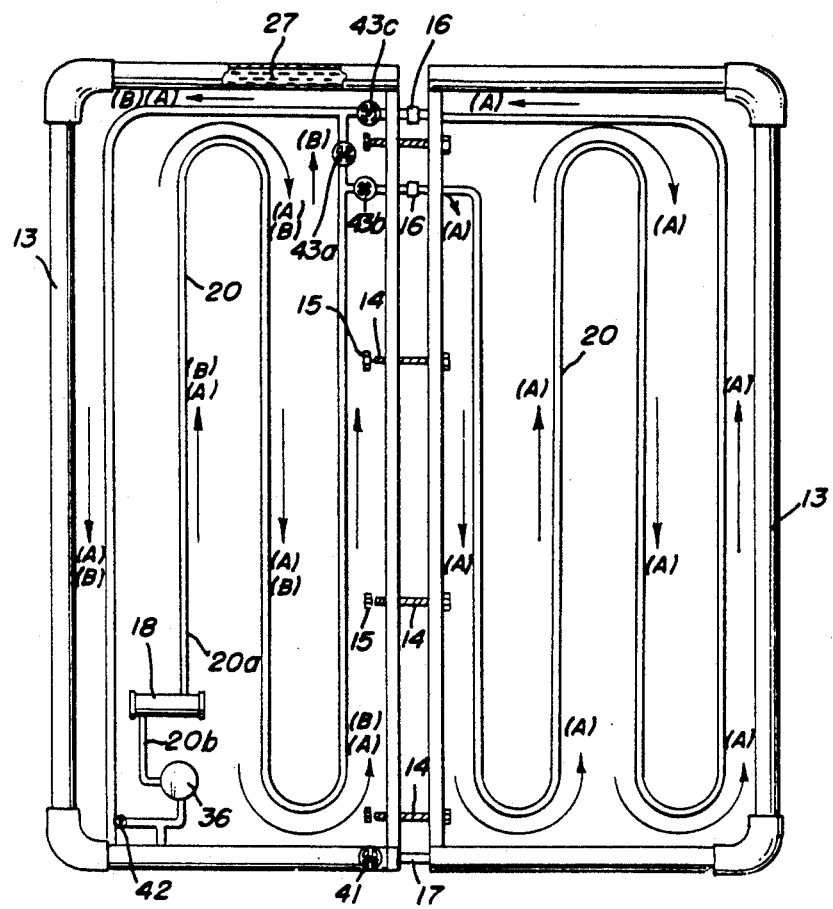
FIG. 2 is a top plan view of a water pipe extending through a base member of a bed of the water heating bed assembly of the present invention.
Figure 3:
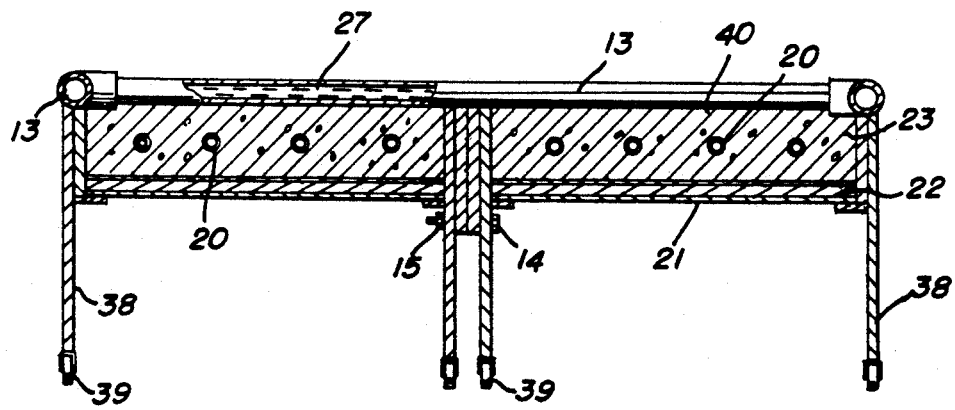
FIG. 3 is a sectional view of FIG. 1, taken along line 3—3.

Referring now in detail to the drawings for the purpose of illustrating preferred embodiments of the present invention, the therapeutic, portable bed assembly provided with a water heating system as shown in FIGS. 1, 2, and 3, which comprises a pair of bed member 10 and 11 for assembling with and disassembling from each other, each bed of the pair of beds 10 and 11 including a base member 12, a serpentine configured water pipe 20 and a U-shaped water tube 13 correspondingly disposed on a circumferential edge of the base member 12. Each bed of the pair of beds 10 and 11 further includes a plurality of bolts 14 and nuts 15 for assembling with and disassembling from the pair of beds 10 and 11, a pair of water pipe connectors 16 for connecting both serpentine configured water pipes 20 of the pair of beds 10 and 11, a U-shaped tube connector 17 for connecting each U-shaped tube 13 of the pair of beds 10 and 11, an electric water heater 18 attached to and disposed within the base member 12 of one of the pair of beds 10 and 11, and a pad member 19 containing mugwort herb, Artemisian vulgaris, whereby the bed having a water heater system can be easily moved and a vapor from the cotton pad 19 can warm and treat the human body lying on the water heating bed.

The base member 12 includes a bottom support member 21, an insulating plate 22 disposed on the bottom support member 21, a concrete plate 23 and a laminated paper cover 24 disposed in sequence on the insulating plate 22, a pair of longitudinal frames 25, and a plurality of transverse frames 26, the longitudinal frames 25 and traverse frames 26 defining a bed support for the insulating plate 22, concrete plate 23 and laminated plate 24.

The U-shaped water tube 13 fixed to the circumferential edge of the beds 10 and 11 through a plurality of clips 46, functions as a water tank and communicates with the serpentine configured water pipe 20 and a security valve 41 disposed on the top thereof for using as a water supply inlet. The serpentine configured water pipe 20 is buried in the concrete plate 23 with a wire net 40.

Figure 4:
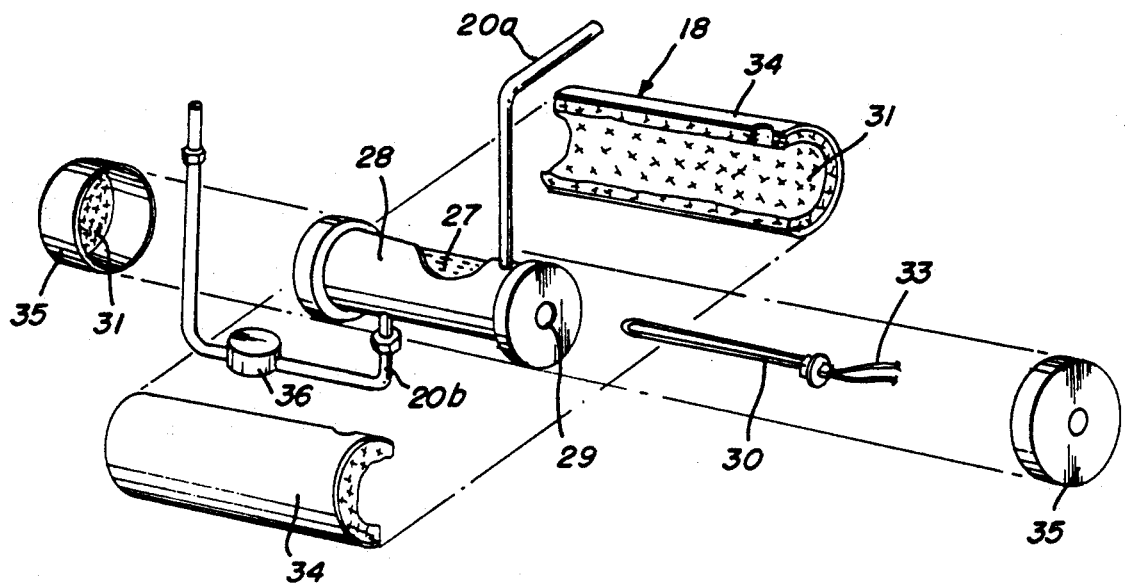
FIG. 4 is a exploded perspective view of a water heater of the water heating bed according to the present invention.
Figure 5:
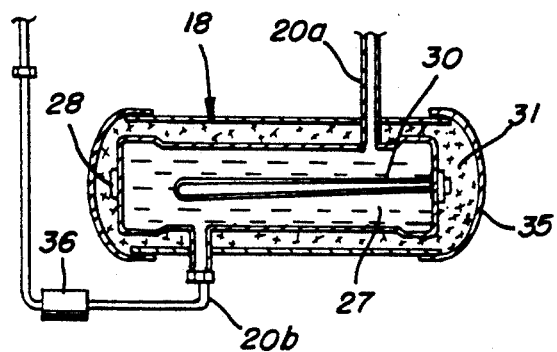
FIG. 5 is a sectional view of the assembled water heater of FIG. 4.

As shown in FIGS. 4 and 5, the water heater 18 includes a cylindrical heater vessel 28 containing water 27, the upper water outlet 20a and the lower water inlet 20b, a thermostat 32 mounted on the cylindrical heater vessel 28, and a central hole 29 for slidably receiving an electric heater 30 with a pair of electric wires 33 which is connected to an on/off switch 37. The water heater 18 is covered by a pair of semi-body covers 34 and a pair of caps 25 with each insulating material 31.

As shown in FIGS. 2, 3, and 4, the water pipe 20 communicates with the cylindrical heater vessel 18 which contains the electric heater 30. In detail, the water pipe 20 disposed within the concrete plate 23 of the base member 11 includes the upper outlet portion 20a which extends from the water heater 18 and extends to the serpentine configured pipe 20 disposed in the base member 11. The serpentine pipe line 20 also includes the lower water inlet 20b which extends from the water heater 18 and also extends to the water pipe 20 through a motor pump 36. The lower water inlet 20b communicates with the U-shaped water tube 13 for retaining water 27 therewithin and is provided with an air valve 42.

The serpentine configured pipe 20 is provided with a first valve 43a, a second valve 43b, and a third valve 43c as an on/off switch valve, disposed on end portions thereof and in the vicinity of the serpentine configured water pipe connectors 16.

As shown in FIG. 1, the separate pad 19 adapted to contain mugwort herb (Artemisian vulgaris) 44 or other pharmaceutical ingredients and provided with a plurality of apertures 45 covers the laminated paper cover 24 for vaporizing the ingredients in the pad 19, whereby upon heating the concrete plate 23 by the water pipe 20 and the laminated paper cover 24 by the water heater 18, the medicinal ingredients from the mugwort herb 44 or other natural or pharmaceutical substance of the pad 19 are evaporated by the heat and may penetrate and treat any desired portion of the human body.

The therapeutic, portable bed assembly according to the present invention includes a plurality of legs 38 with a roller 39 for easily moving from here to there.

According to the present invention, the therapeutic, portable water heating bed assembly operates as follows:

Prior to use of this device, the water tank 13 is filled with water 27 as shown in FIG. 1 and the pad 19 is pre-wetted. When a plug (not shown) is connected to a power source, the pre-wetted pad 19 is heated by the water heater 18 through the serpentine configured water pipe 2 extending through the concrete plate 23 of the base member 12. The vapor evaporates from a plurality of apertures 45 of the pad 19 so as to directly penetrate any desired region of the human body. The heat energy and pressure simultaneously act to treat the effected portion.

When the pair of beds 10 and 11 are assembled with each other, the plurality of bolts 14 and nuts 15 are utilized to fix one bed 10 to the other bed 11. At this time, the pair of pipe connectors 16 are utilized to connect the pair of pipe ends of the bed 10 to the other pair of pipe ends of the bed 11. Also, the tube connector 17 is utilized to connect one tube end of the bed 10 to the other tube end of the bed 11.

Accordingly, when the warm water circulation is performed by being in an on position of the second and third switch valves 43b and 43c and simultaneously in an off position of the first switch valve 43a, the warm water circulates in the direction indicated by arrow (A) shown in FIG. 2. At this time, it is better for the tube connector 17 to be in an open position.

If necessary, when the warm water circulation is performed by being in an off position of the second and third switch valves 43b and 43c and simultaneously in an on position of the first switch valve 43a, the warm water circulates in the direction indicated by arrow (B) shown in FIG. 2. At this time, it is better for the tube connector 17 to be in a closed position. Therefore, if necessary, the pair of beds 10 and 11 or one of them can be operated by operation of first, second and third switch valves 43a, 43b and 43c.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A therapeutic, portable bed assembly provided with a water heating system, comprising:

a pair of beds for assembling and disassembling with each other, each bed of said pair of beds including:

a base member having a bottom support member, an insulating plate disposed on said bottom support member, a concrete plate and a laminated paper cover disposed in sequence on said insulating plate, a pair of longitudinal frames, and a plurality of transverse frames, said longitudinal frames and said traverse frames defining a bed support for said insulating plate, concrete plate and laminated plate, a serpentine configured water pipe extending through said concrete plate of the base member, and a U-shaped tube disposed on a circumferential edge of said base member, said U-shaped tube functioning as a water tank and communicating with said serpentine configured water tube, connecting means for assembling and disassembling said pair of beds, a pair of serpentine configured water pipe connectors for connecting both serpentine configured water pipes of said pair of beds, a U-shaped tube connector for connecting each U-shaped tube of said pair of beds, an electric water heater attached to and disposed within said base member of one of said pair of beds, said electric water heater communicating with said serpentine configured water tube, said electric water heater being provided with a cylindrical heater body adapted to contain water and for slidably receiving an electric heater therewithin and a water heater cover defining a pair of semi-body covers and a pair of caps for covering the cylindrical heater body therewithin, and a pad member containing mugwort herb, *Artemisian vulgaris*, and disposed on said laminated paper cover, whereby the bed having a water heater system can be easily moved and a vapor from the pad member can warm and treat a human body lying on the water heating bed.

2. The therapeutic, portable bed of claim 1, wherein said water pipe is buried in said concrete plate with a wire net.

3. The therapeutic, portable bed of claim 1, wherein said U-shaped water tank is provided with a security valve disposed on the top thereof.

4. The therapeutic, portable bed of claim 3, wherein said security valve is used as a water supply inlet.

5. The therapeutic, portable bed of claim 1, wherein said water heater cover includes an insulating material disposed therein.

6. The therapeutic, portable bed of claim 1, wherein said serpentine configured water pipe is provided with a plurality of valves disposed on end portions thereof and in the vicinity of said serpentine configured water pipe connectors for closing and opening thereof.

7. The therapeutic, portable bed of claim 1, wherein said serpentine configured water pipe is provided with a water pump for accelerating the circulation of water therewithin.

8. The therapeutic, portable bed of claim 1, wherein said connecting means is bolts and nuts.

* * * * *